US011298393B2

(12) United States Patent
Olsen

(10) Patent No.: US 11,298,393 B2
(45) Date of Patent: Apr. 12, 2022

(54) COMPOSITION COMPRISING A MIXTURE OF AN EXTRACT AND BENTONITE

(71) Applicant: Jens Steen Olsen, Havdrup (DK)

(72) Inventor: Jens Steen Olsen, Havdrup (DK)

( * ) Notice: Subject to any disclaimer, the term of this patent is extended or adjusted under 35 U.S.C. 154(b) by 122 days.

(21) Appl. No.: 16/306,199

(22) PCT Filed: Jun. 2, 2017

(86) PCT No.: PCT/DK2017/050183
§ 371 (c)(1),
(2) Date: Nov. 30, 2018

(87) PCT Pub. No.: WO2017/207010
PCT Pub. Date: Dec. 7, 2017

(65) Prior Publication Data
US 2021/0228669 A1 Jul. 29, 2021

(30) Foreign Application Priority Data

Jun. 3, 2016 (DK) .............................. PA201670397

(51) Int. Cl.
| | |
|---|---|
| *A61K 36/00* | (2006.01) |
| *A61K 36/48* | (2006.01) |
| *A61K 8/9789* | (2017.01) |
| *A61P 31/04* | (2006.01) |
| *A61K 8/04* | (2006.01) |
| *A61K 8/21* | (2006.01) |
| *A61K 8/25* | (2006.01) |
| *A61K 8/34* | (2006.01) |
| *A61K 8/46* | (2006.01) |
| *A61K 8/73* | (2006.01) |
| *A61K 9/00* | (2006.01) |
| *A61K 9/06* | (2006.01) |
| *A61K 9/16* | (2006.01) |
| *A61K 35/02* | (2015.01) |
| *A61K 47/02* | (2006.01) |
| *A61K 47/20* | (2006.01) |
| *A61K 47/26* | (2006.01) |
| *A61K 47/38* | (2006.01) |
| *A61Q 11/00* | (2006.01) |

(52) U.S. Cl.
CPC ................ *A61K 36/48* (2013.01); *A61K 8/04* (2013.01); *A61K 8/21* (2013.01); *A61K 8/25* (2013.01); *A61K 8/345* (2013.01); *A61K 8/466* (2013.01); *A61K 8/731* (2013.01); *A61K 8/9789* (2017.08); *A61K 9/0056* (2013.01); *A61K 9/06* (2013.01); *A61K 9/16* (2013.01); *A61K 35/02* (2013.01); *A61K 47/02* (2013.01); *A61K 47/20* (2013.01); *A61K 47/26* (2013.01); *A61K 47/38* (2013.01); *A61P 31/04* (2018.01); *A61Q 11/00* (2013.01); *A61K 2236/10* (2013.01); *A61K 2236/33* (2013.01); *A61K 2236/51* (2013.01); *A61K 2800/70* (2013.01); *A61K 2800/84* (2013.01); *A61K 2800/92* (2013.01)

(58) Field of Classification Search
CPC ....................................................... A61K 36/48
See application file for complete search history.

(56) References Cited

U.S. PATENT DOCUMENTS

| | | | |
|---|---|---|---|
| 9,107,920 B2 * | 8/2015 | Olsen | ..................... A01N 65/20 |
| 2003/0068358 A1 | 4/2003 | Frater-Schroder et al. | |
| 2007/0031512 A1 | 2/2007 | Hughes | |

FOREIGN PATENT DOCUMENTS

| | | | |
|---|---|---|---|
| CN | 104940159 A | * | 9/2015 |
| CN | 105238306 A | | 1/2016 |
| DE | 202013000446 U1 | | 10/2013 |
| IN | 201302979 I3 | * | 10/2015 |
| WO | 2005030279 A1 | | 4/2005 |
| WO | 2007140277 A1 | | 12/2007 |
| WO | 2008125120 A2 | | 10/2008 |
| WO | 2014053262 A1 | | 4/2014 |
| WO | 2014075676 A1 | | 5/2014 |

OTHER PUBLICATIONS

Danish Patent and Trademark Office, Search Opinion. Application No. PA201670397, dated Jan. 3, 2017, 2 pages.
N.N., "Cleanse Kit Instructions", Jan. 1, 2015, XP055395318, retrieved from the internet, URL: http://members.summerbock.com/wp-content/uploads/2015/09/PPC-Cleanse-Kit_Instructions1.pdf, retrieved Aug. 2, 2017, 4 pages.
International Search Report, Application No. PCT/DK2017/050183, dated Aug. 18, 2017, 3 pages.

* cited by examiner

*Primary Examiner* — Qiuwen Mi
(74) *Attorney, Agent, or Firm* — Ziegler IP Law Group, LLC

(57) ABSTRACT

A composition including a mixture of *Trigonella foenum-graecum* extract and bentonite. The mixture is applicable in several technological fields, including the pharmacological, cosmetic, and veterinary field. Notably, the composition is useful in the treatment of a viral infection. The composition is synergistic in the sense that the mixture of *Trigonella foenum-graecum* extract and bentonite has a higher efficiency than each of the components alone.

15 Claims, 4 Drawing Sheets

COMPOSITION COMPRISING A MIXTURE OF AN EXTRACT AND BENTONITE

FIELD

The aspects of the disclosed embodiments relate to a composition comprising a mixture of *Trigonella foenum-graecum* extract and bentonite. The mixture is applicable in several technological fields, including the pharmacological, cosmetic, and veterinary field. Notably, the composition of the aspects of the disclosed embodiments is useful in the treatment of a viral infection. The bentonite of the composition increases the effect of the *Trigonella foenum-graecum* extract. In a certain aspect, the composition is synergistic in the sense that the mixture of *Trigonella foenum-graecum* extract and bentonite has a higher efficiency than the additive effect of each of the components alone.

BACKGROUND

*Trigonella foenum-graecum* (also termed Fenugreek or TFG herein) is an annual herb belonging to the legume family. TFG seed is a major constituent of curry and a part of traditional Indian and Asian cooking. TFG is considered safe as a human food component, taste enhancer, and coloring agent. The TFG seed are rich in phytochemicals, including proteins, steroidal saponin, flavanoids, tannic acids, stearic acid, vegetal oils, alkaloide trigonelline and 4-hydroxyisoleucine (Duke, 2001; Skaltsa, 2002).

Folkloric tales and ancient and traditional medicine has described many uses for TFG seeds and TFG extracts, including lactation stimulation, condiment, aid of labor, indigestion, improvement of general health, and improve metabolism (Basch et al., 2003; Ulbricht et al., 2007). In vitro studies have shown that a TFG seed extract may both induce apoptosis and cell death and have protective effects. TFG extracts protects Chang liver cells against ethanol-mediated toxicity (Kaviarasan et al., 2006) but TFG extracts may also induce apoptosis and cell death in the cell line H-60, primarily via steroid components (Hibasami et al., 2003). Anti-microbial activity of TFG extracts has been reported. Extracts from TFG sprouts has been shown to have in vitro anti-bacterial affect against the stomach bacteria *Helicobacter pylori* (Randhir et al., 2004; Randhir & Shetty, 2007).

A method for preparation of an extract from *Trigonella foenum-graecum* may be found in WO 08/125120. According to the disclosure of the prior art publication, seeds of *Trigonella foenum-graecum* are submerged in water to initiate sprouting before the extraction.

Bentonite is an absorbent aluminium phyllosilicate clay found many places on Earth. Bentonite is known in folklora as "healing clay", which finds varies uses in the health and cosmetic field, including shampoo, deodorant, facial mask, toothpaste, detox bath, baby powder, treatment of burns, bug bites, digestive issues, food poisoning, allergies, diarrhea, arthritis, parasites, anemia, ulcer, eczema, psoriasis, chicken pox, cataract, etc.

The aspects of the disclosed embodiments are directed to obtaining a composition comprising *Trigonella foenum-graecum* extract with an improved anti-viral activity.

SUMMARY

The aspects of the disclosed embodiments are directed to a composition comprising a mixture of *Trigonella foenum-graecum* extract and bentonite. It has surprisingly turned out that said mixture provides for an improved anti-viral activity due to a synergistic behavior of the mixture of *Trigonella foenum-graecum* extract and bentonite. Thus, in a preferred embodiment, the present invention relates to a pharmaceutical composition comprising a mixture of *Trigonella foenum-graecum* extract and bentonite.

The aspects of the disclosed embodiments also relate to the use of the composition in a method for treatment of the human or animal body by surgery or therapy.

Furthermore, the aspects of the disclosed embodiments relate to a composition for use in prevention or treatment of a viral infection.

Extract

One aspect of the disclosed embodiments relates to the preparation of an extract of plant material of a least one plant of the genus *Trigonella*. In the preferred embodiment said plant material is seeds obtained from *Trigonella foenum-graecum*.

The method of preparing said extract according to the aspects of the disclosed embodiments comprises:
a. preparing a blend of plant material and liquid,
b. incubating said blend for at least 3 hours,
c. heating of said blend,
d. recovering a liquid extract from blend e.g. by separating remaining plant material from the blend.

The plant material may be fresh, frozen, dried seeds, or combinations thereof. In the preferred embodiment the plant material is seeds of *Trigonella foenum-graecum*, most preferably dried seeds of said plant.

In order to facilitate the extraction of the active ingredients of the plant material, said plant material is soaked in a liquid, preferably water. The blend of liquid and plant material is incubated for at least 3 hours, more preferably at least 6 hours, preferably at least 12 hours, such as at least 24 hours. The incubation is usually performed at temperatures between 0 and 45° C., suitably at temperatures between 10 and 40° C. The incubation should preferably continue at least until the sprouting is visible.

Subsequently, the blend comprising the plant material soaked in a liquid is heated, preferably to a temperature above the coagulation of proteins. In a certain aspect the blend is boiled.

The blend comprises plant material and a liquid. The ratio by weight of said plant material and said liquid in said blend is suitably 1 to 1, or preferably less plant material by weight such as 1 to 2, or less plant material by weight such as 1 to 3, or less plant material by weight such as 1 to 4, or less plant material by weight such as 1 to 5, or less plant material by weight such as 1 to 6, or less plant material by weight such as 1 to 7, or less plant material by weight such as 1 to 8, or less plant material by weight such as 1 to 9, or less plant material by weight such as 1 to 10. In a preferred embodiment the ratio by weight of said plant material and said liquid is 1 to 6.

During the heating of the blend additional liquid may be added at least once in order to compensate for evaporated liquid and liquid taken up by the plant material. The liquid is heated for at least 5 minutes, such as 10 to 45 minutes, more preferably 20 to 30 minutes, such as 20 minutes. The heating may be terminated when the embryo is released from the seeds, which is associated with increased viscosity of the blend. Suitably, the heating is not continued more than 10 minutes after the embryo has been released.

In one embodiment, the blend is frozen (preferably at −18° C.) prior to or after the heating step for at least 3 hours, preferably more than 6 hours, such as 12 hours, or more than 12 hours. Subsequently, the blend may be subjected to a second round of heating before recovery of the extract, e.g. by removing the remaining plant material. The freezing step is anticipated further to enhance the release of the active ingredients from the plant material.

The volume of a final concentrated extract originating from ½ kg of plant material such as seeds is approximately 2 litres.

For conservation the extract may be refrigerated. Depending on the application the extract may be diluted in water or used as it is. The extract may be further concentrated by removal of solvent. The solvent may be removed or reduced by any appropriate means, such as membrane filtration, evaporation, precipitation, extraction, azeotrope distillation, lyophilisation, spray drying and combinations thereof. The spray dried particles may subsequently be post-dried in a fluid bed apparatus.

The aqueous extract of *Trigonella foenum-graecum* has a tendency to smell of sotolon. The smell may be considered unpleasant by some uses and may therefore restrict the application of the extract. The present inventors have surprisingly found that the amount of sotolon may be reduced drastically by spray drying the extract. Therefore, in a preferred aspect of the embodiments, the aqueous extract is dried by spray drying.

The extract of the disclosed embodiments may be purified to isolate the active ingredient(s) by any appropriate method. Thus, the extract may be fractioned using gel filtration, HPCL, extraction, precipitation, etc. In a presently useful method the extract is fractioned using HPLC. In a specific method the active ingredient(s) is included in an extract fraction obtainable by performing reverse phase chromatography on a size B Lichroprep RP-18 (40-63 μm) (Merck) of the basis extract using the following gradient: 0-1 min $H_2O$/AcN 98:2, then using a steady gradient from 1-40 min going to 100% and collecting the fraction at the time interval between 5 and 10 min. The solvent of the purified extract may be removed or reduced by any of the methods disclosed above. In an aspect of the embodiments, the purified extract is spray dried.

In another specific purification method the aqueous extract may initially be treated with ethanol to precipitate the majority of the plant residues and polysaccharides from the extract. The precipitate may be removed by sedimentation or centrifugation. For easier storage, the solvent may be evaporated or otherwise removed so as to produce a powder. Alternatively the ethanol treated extract may be used directly in the subsequent process. The powder may subsequently be suspended in water and acidified to pH 1-4, preferably pH 2, with a strong acid such as hydrochloric acid. The acidified extract is extracted with a organic water immiscible solvent like heptane. After agitation the organic and the aqueous layer are separated and the aqueous layer is treated with an alkaline agent to obtain a pH above pH 9, preferably around pH 10. The alkaline aqueous phase is again extracted with an organic water immiscible solvent and agitated. A solid powder is obtained from the recovered organic phase by removing the solvent by evaporation, such as by evaporation under reduced pressure or spray drying.

Bentonite

Bentonite is an absorbent aluminum phyllosilicate clay. Bentonite is usually formed from weathering or diagenesis of volcanic ash. The different types of bentonite are generally named after the dominant ion, i.e. sodium bentonite, potassium bentonite, aluminum bentonite, iron bentonite, and calcium bentonite. Sodium and calcium bentonite are generally preferred.

Sodium bentonite is characterized by a high swelling power, often absorbing as much as several times its dry mass in water. Calcium bentonite is an adsorbent of ions and other components, and is characterized by a somewhat lower swelling power. Calcium bentonite may have the calcium ion exchanged with the sodium ion to convert it to sodium bentonite (termed sodium benefication of sodium activation) to exhibit many of sodium bentonite's properties by an ion exchange process. This transformation can be accomplished by adding a soluble sodium compound to the Ca-bentonite.

As bentonite is a naturally occurring clay, it may contain a complex blend of components. In general, the bentonite of the aspects of the disclosed embodiments comprises smectite clay. The smectite may e.g. be selected among montmorillonite, beidellite, sauconite, stevensite hectorite, saponite, nontronite, vermiculite, and mixtures thereof. Also present in the bentonite clay may be kaolin, illite, and/or chlorite. The amount of smectite in the bentonite is generally above 50% by weight, such as above 70% by weight, and suitably above 80% by weight.

Smectite is defined in clay mineralogy as a 2:1 clay—consisting of an octahedral sheet sandwiched between two tetrahedral sheets. Smectites are comprised of layers of negatively charged aluminosilicate sheets held together by charge-balancing counter-ions such as $Na^+$ and $Ca^{2+}$. In the presence of water these cations tend to hydrate, thereby forcing the clay layers apart in a series of discrete steps. This causes the smectite to swell.

It will be understood that the bentonite used in the composition of the aspects of the disclosed embodiments may be naturally occurring and unmodified bentonite, or any fraction thereof enriched in a certain component and optionally chemically modified, especially by exchange of ions. Montmorillonite is hydrated sodium calcium aluminum magnesium silicate hydroxide having the formula $(Na,Ca)_{0.33}(Al,Mg)_2(Si_4O_{10})(OH)_2.nH_2O$. In one embodiment the bentonite clay is montmorillonite.

In aqueous environments, each smectite particle is composed of a multitude of submicroscopic platelets stacked in sandwich fashion with a layer of water between each. A single platelet is about one nanometer thick and up to several hundred nanometers across. Once the clay is hydrated, the weakly positive platelet edges are attached to the negatively charged platelet faces. A three dimensional colloidal structure forms, which accounts for the characteristic rheology imparted by these clays, i.e. an increase in viscosity. Without wishing to be bound by any theory it is presently believed that the colloidal structure is of particularly value for its ability to trap and segregate vira in aqueous suspension.

The amount of smectite in the composition is generally not above 50% by weight. For most practical purposes, an amount of approximately 30% by weight or less of bentonite clay is used to avoid a viscosity, which is not desirable from an end-user point of view. Suitably, the amount of smectite is 10% by weight or less, such as 5% by weight or less. To obtain a microorganism reducing effect even a small amount of bentonite is suitable. In general, the amount of smectite is 0.0001% by weight or above, such as 0.001% by weight, 0.01% by weight, 0.1% or above and preferably 0.3% by weight and above.

Bentonite clays are commercially available under various trade names including Van Gel B, Veegum, Veegum F, Veegum HV, VeegumK, Veegum HS, Veegum Ultra, Veegum D, Veegum Pure, Veegum Ultra, Veegum PRO, Veegum plus, Veegum T, Van Gel B, Van Gel C, Van Gel ES, Van Gel O, all trademarks of R.T. Vandebilt Company. Bentonite clays are also available from Amcol International.

Smectite clay may also be provided synthetically e.g. following the method of Nakazawa, H., Yamada, H., and Fujita, T. (1992): Crystal synthesis of smectite applying very high pressure and temperature, *Applied Clay Science*, 6, 395-401.

Bentonite occurs in many geological areas of the world. According to British Geological Survey bentonite is produced in at least 44 countries. Thus, sodium bentonite is i.a. produced in USA in South Dakota and in Wyoming. Sodium bentonite is also produced in Turkey in the Tokat Rødby region. Mixed sodium/calcium bentonite is mined in Greece, Australia, India, Russia and Ukraine. Calcium bentonite is mined in Mississippi and Alabama, Germany, Greece, Turkey, India, and China. In a certain aspect of the embodiments a bentonite produced in Denmark near Rødby is preferred.

The *Trigonella foenum-graecum* extract and bentonite may be mixed in any proportion that provide the intended effect. In a certain aspect of the embodiments the *Trigonella foenum-graecum* extract to bentonite is mixed in a weight ratio between 1:10 to 10:1. Suitably, the weight ratio between *Trigonella foenum-graecum* extract to bentonite is at least 2:10, such as 3:10. Similarly, the weight ratio of bentonite to *Trigonella foenum-graecum* extract is preferably at least 2:10, such as 3:10. In a preferred aspect the weight ratio between *Trigonella foenum-graecum* extract to bentonite is between 4:10 and 10:4.

Formulation

The composition may comprise a variety of further components for making up the final formulation. According to a certain aspect of the disclosed embodiments the weight of the mixture of *Trigonella foenum-graecum* extract and bentonite is at least 0.01% by weight of the final formulation, such as at least 0.05% by weight and suitably at least 0.1% by weight.

The formulation will generally be useful for application to the human body in products categorized as foods, dietary supplements, pharmaceuticals, cosmetics, medical devices, etc. In accordance with a certain aspect of the disclosed embodiments, the composition can be a pharmaceutical formulation. The mixture according to the disclosed embodiments may be formulated in any form and together with any appropriate pharmaceutically or food acceptable additive.

The pharmaceutical composition comprising a mixture according to the disclosed embodiments may be formulated in a number of different manners, depending on the purpose of the particular medicament and the type of administration. It is well within the scope of a person skilled in the arts to formulate compositions that are in accordance with the preferred type of administration.

The composition comprising the extract and bentonite according to the disclosed embodiments may be prepared by any conventional technique, e.g. as described in Remington: The Science and Practice of Pharmacy 1995, edited by E. W. Martin, Mack Publishing Company, 19th edition, Easton, Pa.

The composition may comprise pharmaceutical acceptable additives such as any conventionally used pharmaceutical acceptable additive, which should be selected according to the specific formulation, intended administration route etc. For example the pharmaceutical acceptable additives may be any of the additives mentioned in Nema et al, 1997. Furthermore, the pharmaceutical acceptable additive may be any accepted additive from FDA's "inactive ingredients list".

One preferred embodiment of the present disclosure is to provide a composition, such as a pharmaceutical or cosmetic composition, formulated for topical application on a local, superficial and restricted area such as a wound, a cold sore, a wart, acne, diaper rash, rectum, genitals, etc. According to the present disclosure, the term topical administration includes mocusal administration.

In said above-mentioned embodiment, the composition may be formulated as an ointment, a lotion, a crème, a bath admixture, a gel, a paste, a milk, a suspension, an aerosol, a spray, a film, a foam, a serum, a swab, a pledget, a pad, mouth wash, a patch, a powder, a paste, a tooth paste, a liniment, viscous emulsion, porridge, liquid, or another formulation which is appropriate for topical administration.

Such compositions for topical administration may further include physiologically acceptable components such as carriers, surfactants, preservatives, stabilizing agents, buffers, excipients and emulsifiers suited for this type of administration. Suitable components for topical delivery systems are preferably chosen from components that do not cause excessive or unavoidable irritation or pain to the recipient. Carriers include diluents and provide the medium in which the pharmaceutical constituents are dissolved, dispersed or distributed.

The composition according to the present disclosure may comprise, but are not restricted to, a carrier such as an aqueous liquid base, nonaqueous liquid base, water soluble gel, a mineral oil base, emulsion, ointment, crème, gel or lotion, suspension of solid particles in a liquid.

The composition of the present disclosure may be applied to skin and the active components may excert their action on the skin or after penetration of the skin. The topical availability of active compounds depend on various factors including their ability to dissolve in the carrier (gel, cream—hydrophilic), and their ability to permeate the skin barrier (i.e., the stratum corneum—hydrophobic), thus requiring a certain hydrophobic-hydrophilic balance. Formulations may require addition of excipients, such as permeation enhancers and solubilizers to facilitate either or both of the transport processes (dissolution into vehicle and diffusion across skin). Additives, such as alcohols, fatty alcohols, fatty acids, mono- di- or tri-glycerides, glycerol monoethers, cyclodextrin and derivatives, polymers, bioadhesives, terpenes, chelating agents and surfactants have been disclosed to increase transdermal delivery of drugs. It is within the aspects of the disclosed embodiments to make use of such excipients.

Any method, not limited to the above-mentioned, for increasing transdermal or transmucosal delivery is within the scope of the present disclosure. The medicament according to the aspects of the disclosed embodiments may therefore comprise surfactants such as ionic and/or non-ionic surfactants. Suitable non-ionic surfactants include for example: fatty alcohol ethoxylates (alkylpolyethylene glycols); alkylphenol polyethylene glycols; alkyl mercaptan polyethylene glycols; fatty amine ethoxylates (alkylaminopolyethylene glycols); fatty acid ethoxylates (acyl polyethylene glycols); polypropylene glycol ethoxylates (Pluronic); fatty acid alkylolamides (fatty acid amide polyethylene glycols); alkyl polyglycosides, N-alkyl-, N-alkoxypolyhydroxy fatty acid amide, in particular N-methyl-fatty acid glucamide, sucrose esters; sorbitol esters, esters of sorbitol polyglycol ethers and lecithin. Ionic surfactants include for example sodium lauryl sulfate, sodium laurate, polyoxyethylene-20-cetylether, Laureth-9, sodium dodecylsulfate (SDS) and dioctyl sodium sulfosuccinate.

Alcohols include, but are not limited to, ethanol, 2-propanol and polyols such as polyethylene glycol (PEG), propylene glycol, glycerol, propanediol.

Methods for enhancing drug delivery through topical administration may be applied with the present disclosure, and include any means of increasing absorption, minimizing metabolism, and/or prolonging the half-life of the active ingredient of the medicament such as the extract of *Trigonella foenum-graecum*. Such means include the use of transporters of the type liposomes, ISCOMs, nano-particles, microspheres, hydrogels, organogels, polymers or other micro-encapsulation techniques.

Another preferred embodiment of the present disclosure is to provide the mixture formulated for oral administration such as a mouth wash. In one preferred embodiment the medicament is formulated as a mouth wash such as by dissolving or dispersing the mixture according to the present disclosure in a liquid.

The liquid may be any useful liquid, however it is frequently preferred that the liquid is an aqueous liquid. It is furthermore preferred that the liquid is sterile. Sterility may be conferred by any conventional method, for example filtration, irradiation or heating.

It is within the scope of the disclosed embodiments to supply a pharmaceutical composition for the treatment of clinical conditions described herein involving an infection or an increased risk of acquiring an infection. For example, but not limited to, clinical conditions involving infection or at risk of being infected by a virus. In one embodiment the mixture of the aspects of the disclosed embodiments is co-administered with at least one second active ingredient. Preferably, said second active ingredient is an antimicrobial substance, for example an antiseptic, antibiotic, antifungal, antiparasitic or antiviral agent.

Preferably, the mixture of the extract of *Trigonella foenum-graecum* and the bentonite is present in the same composition. Alternatively, they may be supplied in a kit of parts, i.e. one part comprises the extract of *Trigonella foenum-graecum* and the other part comprises the bentonite.

In an embodiment according to the present disclosure, the mixture of the disclosed embodiments is a constituent in a tooth-paste.

According to the aspects of the disclosed embodiments the compound is preferably present in "a pharmaceutical effective dosage" of the composition. A pharmaceutical effective dosage refers to the amount necessary to induce the desired biological effect on the subject in need of treatment. Furthermore, the expression pharmaceutical effective dosage covers medical effective dosage and cosmetic effective dosage.

The composition according to the aspects of the disclosed embodiments may be administrated once or more than once a day, for example it may be administered in the range of 2 to 10 times a day, such as 2 to 7 times, for example 2 to 5 times, such as 2 to 4 times, such as 2 to 3 times a day.

The composition according to the aspects of the disclosed embodiments may be administrated to the subject for a period of treatment of one or more than one week such as two weeks, three weeks, four weeks, five weeks, six weeks, seven weeks, eight weeks or more than eight weeks. The treatment may be repeated on subjects who relapse.

Diseases Treated

The mixture of compounds of the aspects of the disclosed embodiments may be used for treatment of a variety of diseases. In a first aspect the compounds of the disclosed embodiments may be used for curing diseases caused by viruses. It is presently believed that viruses having a lipid envelope membrane are especially susceptible to the compounds of the aspects of the disclosed embodiments. Examples of such viruses include herpes simplex virus (HSV), influenza virus, human papilloma virus (HPV) or human immunodeficiency virus (HIV).

In another aspect of the disclosed embodiments the compounds may be used for treating diseases requiring a proliferation of cells. Such diseases include: wounds, such as a surgical wounds or burns, mouth cavity diseases, cold sores, or periodontal diseases.

The compounds described herein may be used for the treatment of various virus related diseases. Viral infection refers to an infection caused by a virus. Unlike bacteria viral replication is dependent on a host cell employing the host systems such as the transcription factor and translational machinery. The most common human diseases caused by viruses include common cold, the flu, cold sores, and warts.

In one embodiment according to the present disclosure a composition as described herein is used in the treatment of viral infections such as common cold, the flu, cold sores, and warts.

Specific examples of virus related diseases which may be treated with the composition described herein include herpes simplex virus (HSV). Herpes simplex virus 1 and 2 (HSV-1 and HSV-2) may be treated with the composition described herein, however, in a preferred aspect of the disclosed embodiments the disease is caused by HSV-2. Both HSV-1 (which produces most cold sores) and HSV-2 (which produces most genital herpes) are ubiquitous and contagious. They can be spread when an infected person is producing and shedding the virus.

Symptoms of herpes simplex virus infection include watery blisters in the skin and/or mucous membranes of the mouth, lips or genitals. Lesions heal with a scab characteristic of herpetic disease. Sometimes, the viruses cause very mild or atypical symptoms during outbreaks. However, as neurotropic and neuroinvasive viruses, HSV-1 and -2 persist in the body by becoming latent and hiding from the immune system in the cell bodies of neurons. After the initial or primary infection, some infected people experience sporadic episodes of viral reactivation or outbreaks. In an outbreak, the virus in a nerve cell becomes active and is transported via the neuron's axon to the skin, where virus replication and shedding occur and cause new sores.

The structure of herpes viruses consists of a relatively large double-stranded, linear DNA genome encased within an icosahedral protein cage called the capsid, which is wrapped in a lipid bilayer called the envelope. The envelope is joined to the capsid by means of a tegument. This complete particle is known as the virion. It is presently believed that an extract compound exerts its action by interactions with the lipid bilayer.

HSV evades the immune system through interference with MHC class I presentation of antigen on the cell surface. It achieves this through blockade of the TAP transporter induced by the secretion of ICP-47[15] by HSV. TAP maintains the integrity of the MHC class I molecule before it is transported via the golgi apparatus for recognition by CD8+ CTLs on the cell surface.

Herpes viruses establish lifelong infections and the virus cannot currently be eradicated from the body. Treatment usually involves general-purpose antiviral drugs that interfere with viral replication, reducing the physical severity of outbreak-associated lesions and lowering the chance of transmission to others. Thus, the composition of the aspects of the disclosed embodiments clearly fulfil a need for the provision of a treatment method more efficient than, or at least an alternative to, the present general-purpose antiviral drugs.

Another disease which may be cured or alleviated by the present composition is influenza. Influenza, commonly known as the flu, is an infectious disease of birds and mammals caused by RNA viruses of the family Orthomyxoviridae, the influenza viruses. The term influenza includes disease caused by either influenza A, influenza B or influenza C virus. The most common symptoms are chills, fever, sore throat, muscle pains, headache (often severe), coughing, weakness/fatigue and general discomfort. Although it is often confused with other influenza-like illnesses, especially the common cold, influenza is a more severe disease caused by a different type of virus. Influenza may produce nausea and vomiting, particularly in children.

Typically, influenza is transmitted through the air by coughs or sneezes, creating aerosols containing the virus. Influenza can also be transmitted by direct contact with bird droppings or nasal secretions, or through contact with contaminated surfaces. Airborne aerosols have been thought to cause most infections, although, which means of transmission is most important is not absolutely clear.

The interior of the influenza virus particles the RNA genome is present and bound to the ribonuclear proteins. A capsid surrounds the genetic material and a lipid envelop is present outside the capsid. Present on the lipid envelope is various proteins including haemmagglutinin and ion channels. Presently it is assumed that an extract compound of the aspects of the disclosed embodiments exert its action by interaction with the lipid membrane.

The compositions of the aspects of the disclosed embodiments may also be used to treat diseases caused by human papilloma virus (HPV). Warts are common benign epidermal lesions associated with human papillomavirus infection (HPV) infection. Warts referrers to a range of conditions, which differs in type of papillomavirus causing the conditions, the morphology, appearance on the body such as on the fingers, the foot, the face such as the lips or near the eyelids, or genital areas. Example of warts include common wart (verruca vulgaris) caused by HPV 1, 2, 4, 27, and 29, flat wart (verruca plana) caused by HPV 3, 10, 28, and 49, filiform or digitate wart, Palmar and plantar wart (verruca, verruca pedis) caused by HPV 1, mosaic wart, and genital wart (venereal wart, condyloma acuminatum, verruca acuminata).

Apart from being painful warts may also be a cosmetic problem there is no effective treatment of warts, which frequently reoccur a few months or years after the available treatment has been terminated.

In a preferred embodiment according to the present disclosure the composition disclosed herein is used for the treatment of warts such as warts located on the fingers, the foot, the face such as the lips or near the eyelids, or genital areas.

In another aspect of the disclosed embodiments, a human immunodeficiency virus (HIV) related disease is treated with the composition disclosed herein. HIV is a lentivirus that causes acquired immunodeficiency syndrome (AIDS), a condition in humans in which progressive failure of the immune system allows life-threatening opportunistic infections and cancers to thrive. HIV includes several sub-types, including HIV-1 and HIV-2.

HIV infects vital cells in the human immune system such as helper T cells (specifically CD4+ T cells), macrophages, and dendritic cells. HIV infection leads to low levels of CD4+ T cells through three main mechanisms: First, direct viral killing of infected cells; second, increased rates of apoptosis in infected cells; and third, killing of infected CD4+ T cells by CD8 cytotoxic lymphocytes that recognize infected cells. When CD4+ T cell numbers decline below a critical level, cell-mediated immunity is lost, and the body becomes progressively more susceptible to opportunistic infections.

The HIV virus particle is roughly spherical with a diameter of about 120 nm, around 60 times smaller than a red blood cell, yet large for a virus. It is composed of two copies of positive single-stranded RNA that codes for the virus's nine genes enclosed by a conical capsid composed of 2,000 copies of the viral protein p24. The single-stranded RNA is tightly bound to nucleocapsid proteins, p7, and enzymes needed for the development of the virion such as reverse transcriptase, proteases, ribonuclease and integrase. A matrix composed of the viral protein p17 surrounds the capsid ensuring the integrity of the virion particle.

This is, in turn, surrounded by the viral envelope that is composed of two layers of fatty molecules called phospholipids taken from the membrane of a human cell when a newly formed virus particle buds from the cell. It is presently believed that an extract component of the aspects of the disclosed embodiments interact with the phospholipid bilayer to exert its action. The specific mode of action is not known presently to the inventors.

The present compositions may be used for treating a variety of diseases and disorders including diseases requiring a proliferation of cells. An example of a disease which may be cured or the symptoms may be alleviated is periodontal diseases. Periodontitis (periodontosis, paradentosis, pyorrhea) is a dental disorder that results from progression of gingivitis, involving inflammation and infection of the ligaments and bones that support the teeth.

Left untreated for years it may result in loss of bone supporting the teeth and final loss of teeth. The conditions may involve one or more teeth.

Gingivitis is associated with little or no discomfort apart from redden, swollen and easily bleeding gums. Gingivitis is often caused by inadequate oral hygiene leaving the bacteria in plaque on the teeth causing the gums to become inflamed. Gingivitis is reversible with professional treatment and good oral home care. If gingivitis is left untreated plaque can spread and grow below the gum line and the condition may advance to periodontitis. Toxin released by bacteria in the plaque initiate an inflammatory response in the gums, which may become chronic and destroy the bone supporting the teeth. Gums separate from the teeth, forming pockets (spaces between the teeth and gums) that become infected. As the disease progresses, the pockets deepen and more gum tissue and bone are destroyed. Often, this destructive process has very mild symptoms. Eventually, teeth can become loose and may have to be removed.

Chronic periodontitis is recognized as the most frequently occurring form of periodontitis. Chronic periodontitis results in inflammation within the supporting tissues of the teeth, progressive attachment and bone loss and is characterized by pocket formation and/or recession of the gums (gingiva). It is prevalent in adults and a major cause of loss of teeth in adults, but the disease can occur at any age. Progression of attachment loss usually occurs slowly, but periods of rapid progression can occur.

Aggressive periodontitis is a condition that affects patients who are otherwise clinically healthy. Common features include rapid attachment loss and bone destruction and familial aggregation. Periodontititis, often with onset at a young age, associated with one of several systemic diseases, such as diabetes or osteoporosis (Periodontitis as a manifestation of systemic diseases). Necrotizing periodontal diseases is another form of infection characterized by necrosis of gingival tissues, periodontal ligament and alveolar bone. This condition is most often associated with systemic conditions including, but not limited to, HIV infection, malnutrition and immunosuppression.

Apart from is bacterial plaque other factors affecting the health of the gums include: Smoking, genetics, pregnancy, puberty, stress, medication, clenching/grinding of teeth, poor nutrition, diabetes and other systemic diseases.

Gingivitis usually disappears with good self-care. In contrast, periodontitis requires repeat professional care. A person using good oral hygiene can clean only 2 to 3 millimetres (1/12 inch) below the gum line. A dentist can clean pockets up to 4 to 6 millimetres deep (1/5 inch) using scaling and root planning, which thoroughly remove tartar and the diseased root surface. For pockets of 5 millimetres (1/4 inch) or more, surgery is often required. A dentist or periodontist may access the tooth below the gum line surgically (periodontal flap surgery) to thoroughly clean the teeth and correct bone defects caused by the infection. A dentist or periodontist may also remove part of the infected and separated gum (a gingivectomy) so that the rest of the gum can reattach tightly to the teeth and the person can then remove the plaque at home. A dentist may prescribe antibiotics (such as tetracyclines or metronidazole), especially if an abscess has developed. A dentist may also insert antibiotic-impregnated materials (filaments or gels) into deep gum pockets, so that high concentrations of the drug can reach the diseased area. Periodontal abscesses cause a burst of bone destruction, but immediate treatment with surgery and antibiotics may allow much of the damaged bone to grow back.

If a patient has 5 millimetres (1/4 inch) or deeper pockets around most of their teeth, then they would then risk loss of all of their teeth over the years. If this not identified and the patient remains unaware of the progressive periodontal disease then, years later, they may be surprised that most of the teeth have suddenly seemed to become loose and that most or all of them may need to be extracted.

Pharmaceutical systemic treatment of gingivitis, periodontitis (aggressive and chronic), periodontitis as a manifestation of systemic diseases, and necrotizing periodontal diseases using tetracyclines is associated with a number of disadvantages the rapid emergence of tetracycline resistant bacterial strains and the occurrence of overgrowth of unsusceptible pathogens, such as Candida, during treatment. Short term treatment of periodontal infection with tetracyclines is often ineffective. Penicillins, which in general are highly effective antimicrobial compositions against anaerobic bacteria, have been shown to be ineffective against bacterial species important in peridental infections (e.g. *P. gingivalis*).

The limitations and disadvantages described above for the currently used surgical and non-surgical therapies reveal the unmet need for effective treatment of these dental conditions.

One highly preferred embodiment according to the present disclosure relates to the use of a composition as described herein for the treatment of a periodontal disease such as gingivitis, periodontitis (aggressive and chronic), periodontitis as a manifestation of systemic diseases, and necrotizing periodontal diseases.

Halitosis (or bad breath) is a very common temporary condition such as "morning breath". Chronic halitosis, which is a more serious and persistent condition, is usually caused by persistent overpopulation of certain types of oral bacteria. Chronic halitosis is often associated with the periodontal diseases described herein.

In one embodiment according to the present disclosure a compound as described herein is used for the treatment of halitosis. In a preferred embodiment said halitosis is chronic halitosis.

In another aspect of the disclosed embodiments the ability to proliferate cells is used to stimulate the treatment of wounds. The term "wound" refers to lesion of skin or mucosa (such as oral mucosa, gastric- and intestinal mucosa). The wound may be a result of an infection, injury, or surgery. Wound according to the disclosed embodiments also include chronic wounds and ulcers.

One preferred embodiment according to the present disclosure relates to the use of a compound as described herein is used for the treatment of or preventing infection of a wound such as a surgical wound, a incised wounds, a penetration wound, a puncture wound, an abrasion, a chronic wound, or an ulcer.

Wounds may also results from bites. Human and mammal (mostly dog and cat, but also squirrel, gerbil, rabbit, guinea pig, and monkey) bites are common and occasionally cause significant morbidity and disability. The hands, extremities, and face are most frequently affected, although human bites can occasionally involve breasts and genitals. In addition to tissue trauma, infection from the biting organism's oral flora is a major concern.

In one embodiment according to the present disclosure a composition as disclosed herein is used for the treatment of bites caused a human or a mammal, preferably a dog.

Wounds treated with the composition according to the aspects of the disclosed embodiments tend to heal faster. In addition scar formation is limited or absent. Scars are areas of fibrous tissue (fibrosis) that replace normal skin after injury and result from the biological process of wound repair in the skin and other tissues of the body. It is presently believed that the increased cell proliferation stimulated by the present compounds of the disclosed embodiments is the explanation for the observed faster healing. In a preferred aspect of the disclosed embodiments, the composition is maintained in close proximity with the wound by a suitable dressing. The dressing ensures that a humid environment is maintained and prolonged so that the active components of the disclosed embodiments may diffuse to the wound and exert is effect. In a preferred aspect the dressing is a surgical dressing with an impermeable backing.

The composition of the present disclosure may in some instances be regarded dual or multiple acting components which may be used for simultaneous addressing the treatment of several diseases such as HIV-1 or HSV-2. Since both HIV-1 and HSV-2 are sexually transmitted, the compounds of the disclosed embodiments may be mixed in a stable solution for topical application. One option is formulation in gels for skin application or as a microbiocide gel to be applied in the vagina or rectum. The latter solution may block or inactivate some sexually transmitted pathogens.

SHORT DESCRIPTION OF THE FIGURES

EXAMPLES

Example 1

Figure 1:
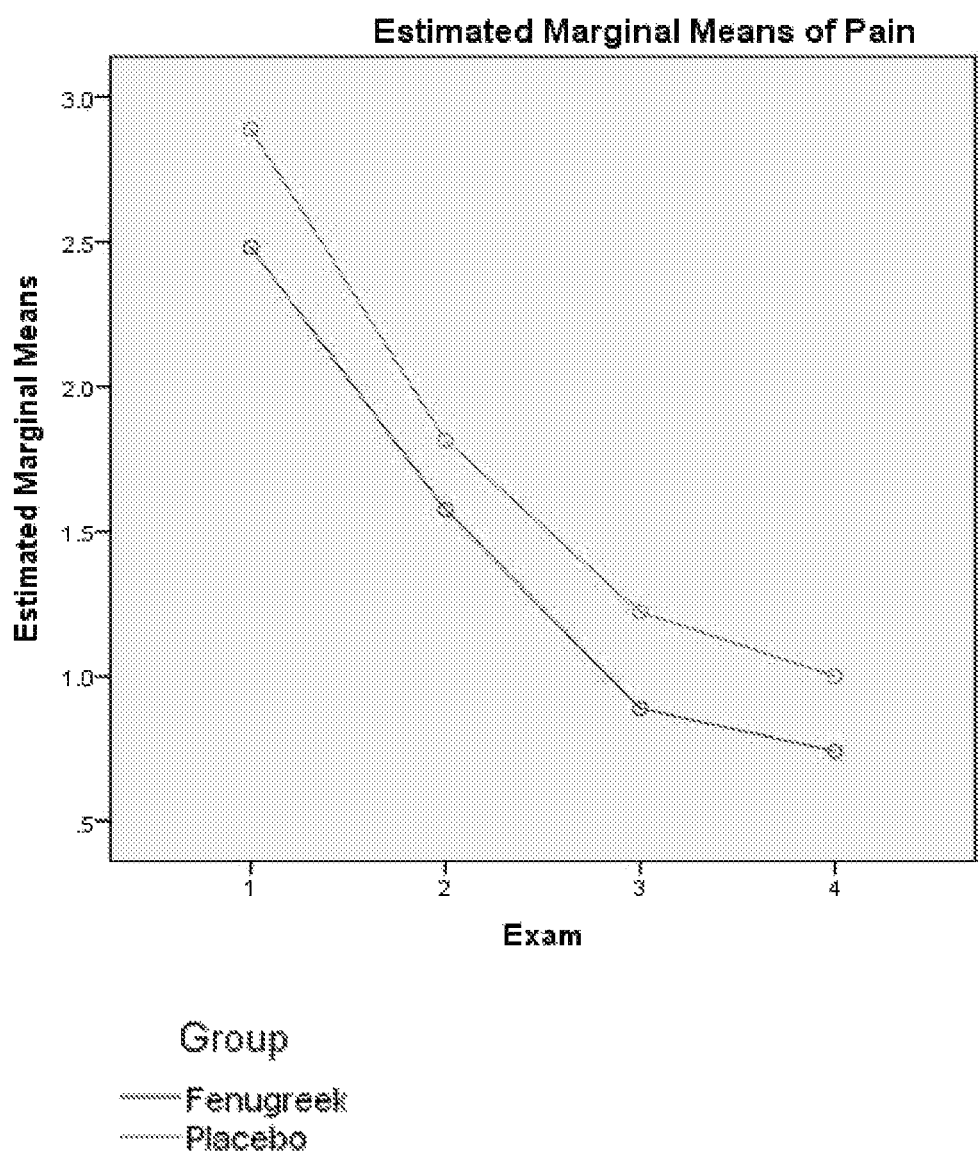
FIG. 1 shows the participants' reporting of pain upon probing, measured on a scale of 1-10.

Preparation of an extract from *Trigonella foenum-graecum* seeds was performed as follows: 500 g seeds of *Trigonella foenum-graecum* were soaked in 2.5 l water for approximately 24 hours. Following the pre-soaking the seeds were cooked for 20 minutes and remains of the seeds were removed from the mixture.

The aqueous extract was freeze dried and a powder was obtained.

Example 2

The aqueous extract of example 1 was spray dried for obtaining a powder in accordance with ISO9001:2008.

The aqueous extract produced in accordance with example 1 had a dry matter content of 2-2.5% by weight and a temperature of 5° C. In a concentrate heater the extract was heated to a temperature of 62° C. prior to spraying by a centrifugal atomizer (GEA Niro) running at 12.500 rpm. The dryer inlet temperature was 170° C. and the dryer outlet temperature was 87° C. The spray dried powder was post-dried in a fluid bed at a temperature of 24° C. The powder moisture content of the dried product was 3.58% by weight and the size of the particles was mainly in the range of 5-30 µm.

Due to the low dry matter of the feed extract, the bulk density of the powder was low, i.e. in the range of 0.08 to 0.1 kg/l. A higher dry matter content of e.g. 15% by weight might have yielded a higher bulk density and larger particles.

It was noted that during the spray drying a major amount of the sotolon present in the aqueous extract was evaporated, which produced a spray dried product deprived of sotolon.

Example 3

Production of an Ointment 250 mg spray dried extract produced in accordance with Example 2 was mixed with 250 mg bentonite obtained from Rødby. The combined mixture was subsequently added to 1 kg of vaseline under agitation.

Example 4

Production of a Tooth Paste 2.5 g spray dried extract produced in accordance with Example 2 was mixed with 2.5 g bentonite obtained from Rødby. The combined mixture was subsequently added to 1 kg of commercially available base tooth paste containing water, hydrated silica, sorbitolpropylene glycol, sodium $C_{14-16}$ olefin sulfonate, aroma, cellulose gum, sodium fluoride, sodium saccharin.

Example 5

Production of a Tooth Paste 25 g spray dried extract produced in accordance with Example 2 was mixed with 25 g bentonite obtained from Rødby. The combined mixture was subsequently added to 1 kg of commercially available base tooth paste containing water, hydrated silica, sorbitol, propylene glycol, sodium $C_{14-16}$ olefin sulfonate, aroma, cellulose gum, sodium fluoride, sodium saccharin.

Example 6

54 persons with gingivitis were enrolled for test of the tooth-paste produced in example 5 in a double-blind, randomized, placebo-controlled, clinical trial.

The test persons were divided in a Fenugreek group and a Placebo group. The Fenegreek group was instructed to brush the teeth with the toothpaste according to example 5 and the Placebo group was instructed to brush the teeth with the base toothpaste not containing fenugreek extract and bentonite. The test persons were examined four times with a week in between. At each examination four parametres were investigated, i.e. pain, gingival bleeding, plaque formation, and gingival inflammation.

FIG. 1 shows the participants' reporting of pain upon probing, measured on a scale of 1-10. It is noticed that the reported pain was less in the group that used the Fenucure Toothpaste compared to the group that used the placebo toothpaste.

Figure 2:
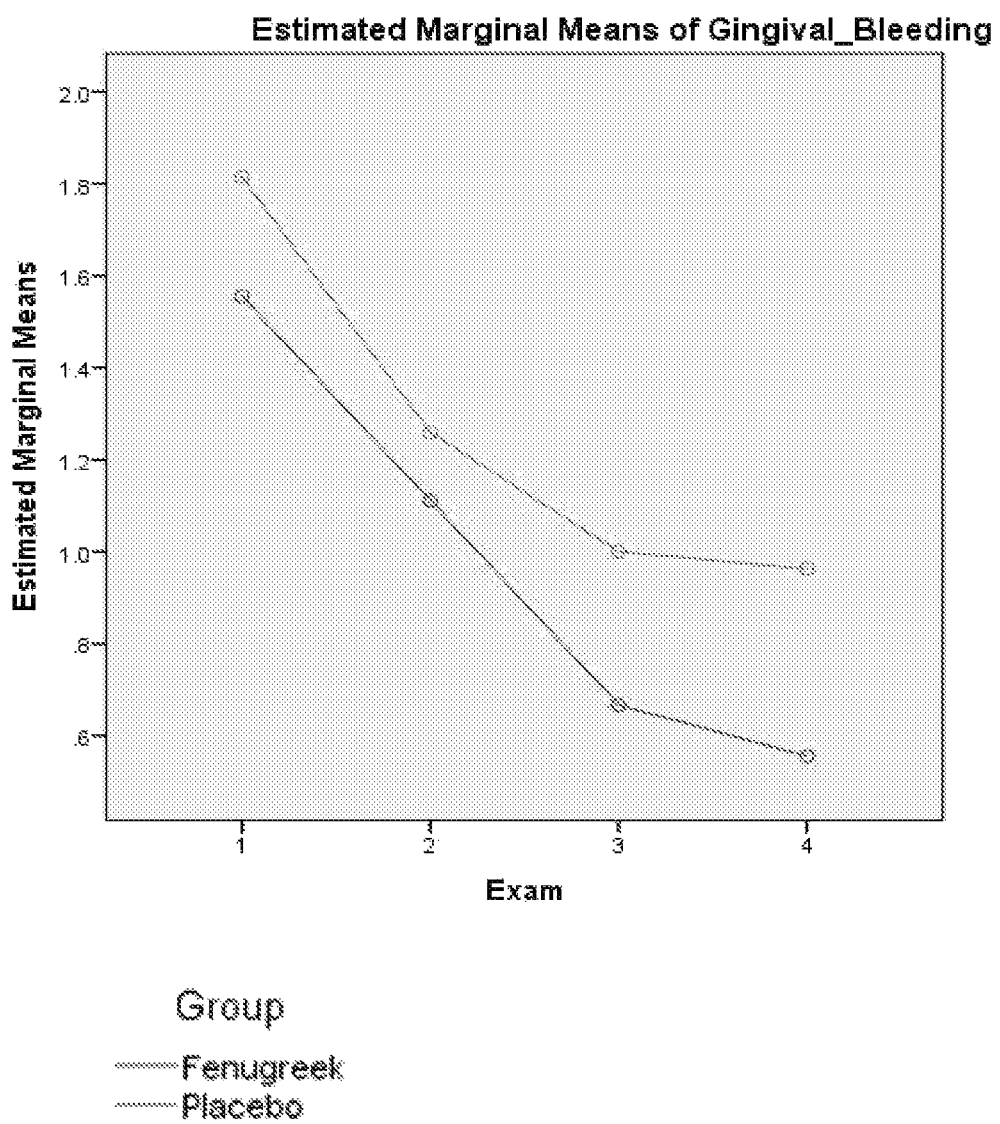
FIG. 2 shows the bleeding upon probing as measured by the Papillary Index of Muhlemann on a scale of 0-4.

FIG. 2 shows the bleeding upon probing as measured by the Papillary Index of Muhlemann on a scale of 0-4. The data shows the bleeding decreased more significantly in the Fenucure Toothpaste group than in the placebo group.

Figure 3:
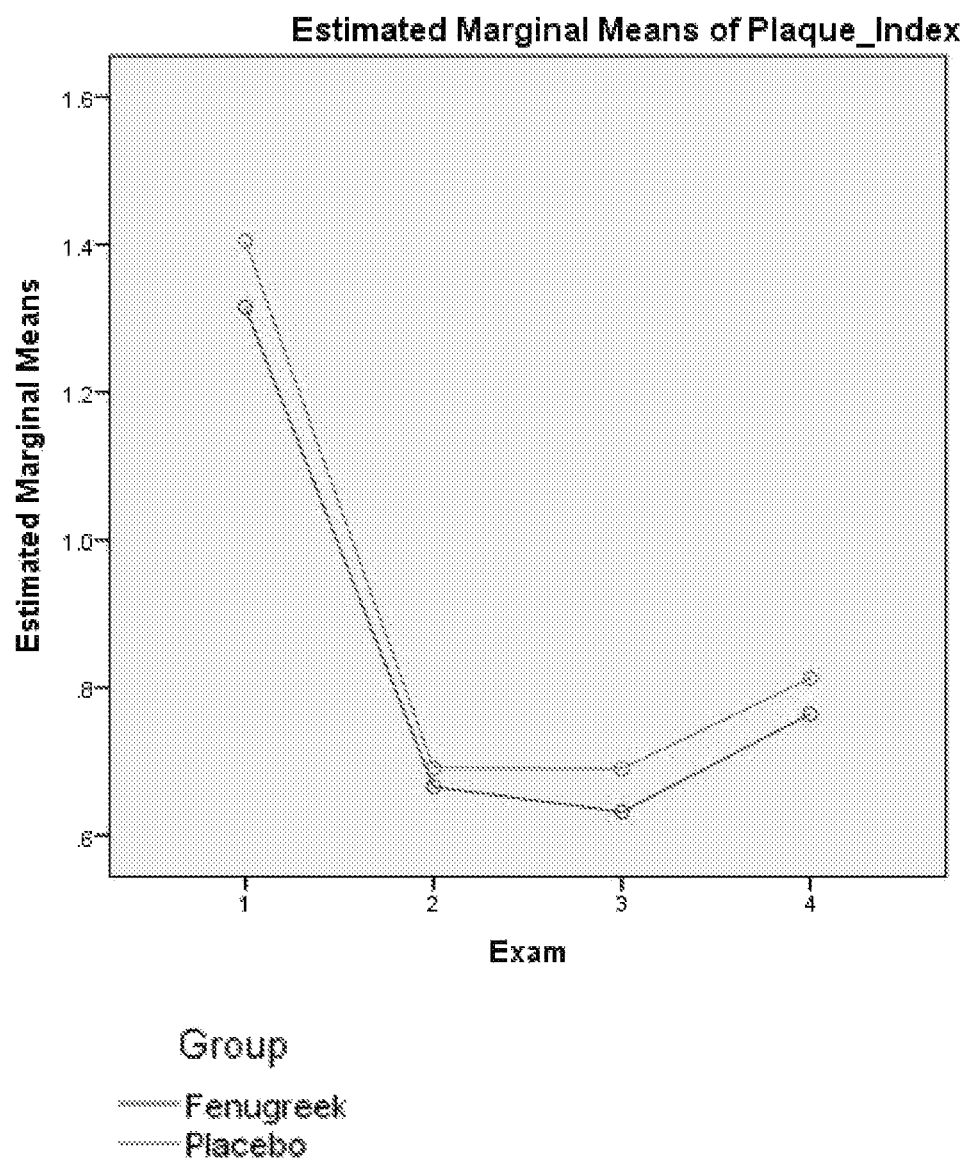
FIG. 3 shows the plaque index.

FIG. 3 shows the plaque index. The amount of plaque was measured according to the following scale:
0—no debris present;
1—soft debris not more than ⅓ of the tooth surface;
2—soft debris ⅓-⅔ of tooth surface and
3—soft debris covering more than ⅔ of tooth.

The test demonstrated a decrease in plaque in the Fenucure Toothpaste group in weeks 2-4 as compared to the group that used the placebo toothpaste.

Figure 4:
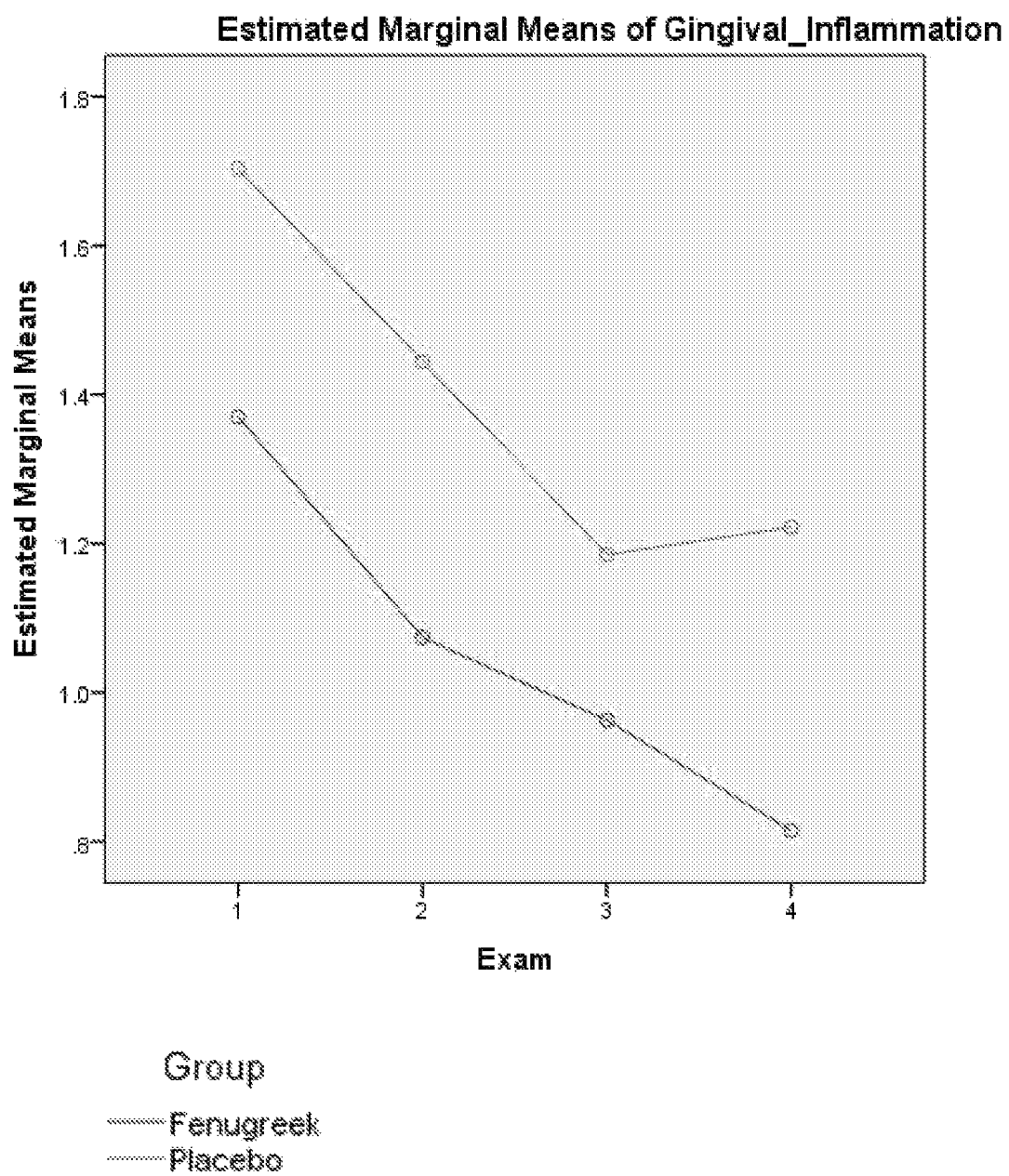
FIG. 4 shows gingival inflammation, as measured weekly by the Gingival Index of Loe and Silness.

FIG. 4 shows gingival inflammation, as measured weekly by the Gingival Index of Loe and Silness. The results of the test showed a consistent decrease weekly in the Fenucure Toothpaste group, while in the placebo group the inflammation decrease was not nearly as significant in weeks 1-3 and inflammation increased in weeks 3-4. Note that the participants had a professional prophylaxis at Week 1.

The invention claimed is:

1. A composition comprising a mixture of *Trigonella foenum-graecum* extract and bentonite with synergistic effect, wherein the *Trigonella foenum-graecum* extract is aqueous and obtainable by the steps of:
   a) preparing a mixture of seeds of *Trigonella foenum-graecum* and liquid,
   b) incubating said mixture for at least 3 hours,
   c) heating of said mixture, and
      recovering a liquid extract from mixture by separating remaining plant material from the mixture.

2. The composition according to claim 1, wherein the incubation in step b) is continued until the sprouting is visible.

3. The composition according to claim 1, wherein the heating of the mixture is conducted at least until the embryo is released from the seeds.

4. The composition according to claim 1, wherein the recovered liquid extract is purified by gel filtration, HPLC, or extraction.

5. The composition according to claim 1, wherein the recovered liquid extract is concentrated by removal of solvent.

6. The composition according to claim 5, wherein the solvent partly or entirely is removed by a method selected among the group consisting of: membrane filtration, evaporation, precipitation, extraction, azeotrope distillation, lyophilisation, spray drying and combinations thereof.

7. The composition according to claim 1, wherein *Trigonella foenum-graecum* extract is spray dried particles.

8. The composition according to claim 1, wherein bentonite comprises 50% by weight or more of smectite.

9. The composition according to claim 8, wherein the smectite is selected among montmorillonite, beidellite, sauconite, stevensite hectorite, saponite, nontronite, vermiculite, and mixtures thereof.

10. The composition according to claim 1, comprising 1:10 to 10:1 by weight dry matter of *Trigonella foenum-graecum* extract to bentonite.

11. The composition according to claim 1, wherein the weight of the mixture of *Trigonella foenum-graecum* extract and bentonite is at least 0.01% by weight of the final formulation.

12. A pharmaceutical composition comprising a mixture of *Trigonella foenum-graecum* extract and bentonite according to claim 1, wherein said pharmaceutical composition is formulated as a gel, cream, mouth-wash, chewing gum, tooth-paste, balm, plaster, lip salve, spray, liquid, ointment, capsule, drop, or tablet.

13. A method for prevention or treatment of a viral infection comprising the step of administering a composition according to claim 1 to a subject in need thereof.

14. The method according to claim 13, wherein said virus is selected from the group of viruses having a lipid membrane.

15. The method according to claim 14, wherein the virus is herpes simplex virus (HSV), influenza virus, human papilloma virus (HPV) or human immunodeficiency virus (HIV).

* * * * *